United States Patent [19]
Ingram et al.

[11] Patent Number: 5,523,228
[45] Date of Patent: Jun. 4, 1996

[54] HYDRODYNAMIC CELL CULTURE ENVIRONMENT FOR THREE DIMENSIONAL TISSUE GROWTH

[75] Inventors: Marylou Ingram, Pasadena, Calif.;
Glenn F. Spaulding, Houston, Tex.;
James J. G. Craft, Pasadena, Calif.;
Chuen P. Ng, Los Angeles, Calif.;
Ramez Saroufeem, Pasadena, Calif.;
Geza B. Techy, Monrovia, Calif.;
Ozkan Yazan, Norwalk, Calif.

[73] Assignee: HMRI/CLMF, Houston, Tex.

[21] Appl. No.: 499,348

[22] Filed: Jul. 7, 1995

[51] Int. Cl.⁶ .................................................. C12N 5/02
[52] U.S. Cl. .................... 435/240.25; 435/240.46; 435/297.1; 435/298.2; 435/303.3; 435/304.1; 435/818
[58] Field of Search ................. 435/297.1, 303.3, 435/298.2, 240.25, 240.3, 240.1, 240.46, 818, 304.1

[56] References Cited

U.S. PATENT DOCUMENTS

| | | | |
|---|---|---|---|
| 3,821,087 | 6/1974 | Knazek et al. | 195/127 |
| 3,946,780 | 3/1976 | Sellers | 150/8 |
| 4,391,912 | 7/1983 | Yoshida et al. | 435/240.25 |
| 4,749,654 | 6/1988 | Karrer et al. | 435/240.21 |
| 4,948,728 | 8/1990 | Stephanopoulos et al. | 435/41 |
| 4,962,033 | 10/1990 | Serkes et al. | 435/240.243 |
| 5,015,585 | 5/1991 | Robinson | 435/240.242 |
| 5,026,650 | 6/1991 | Schwarz et al. | 435/297.1 |
| 5,057,428 | 10/1991 | Mizutani et al. | 435/293.2 |
| 5,153,131 | 10/1992 | Wolf et al. | 435/240.24 |
| 5,330,908 | 7/1994 | Spaulding | 435/240.24 |

*Primary Examiner*—David A. Redding

[57] ABSTRACT

A cell culture chamber with a novel hydrodynamic environment, constructed with gas permeable membranes is disclosed. The culture chamber is horizontally rotated, wall movement suspends cells and enhances oxygen mass transfer as cells aggregate and grow into 3-dimensional tissue.

7 Claims, 1 Drawing Sheet

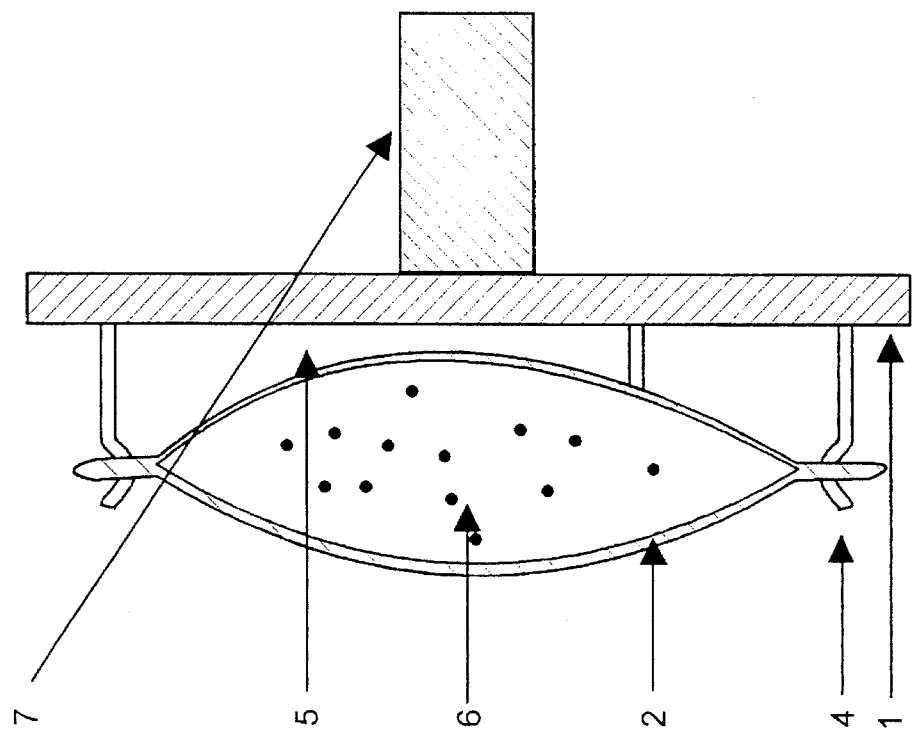
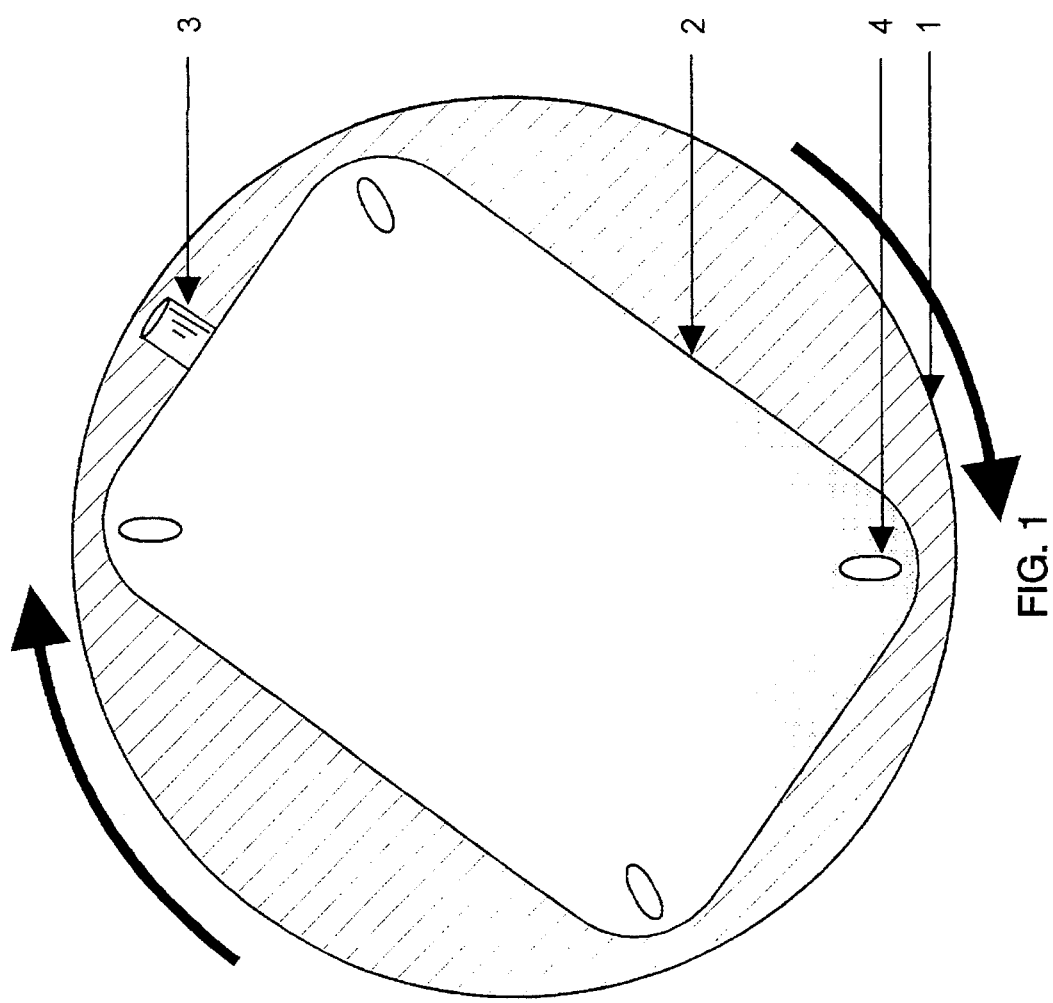
FIG. 2
FIG. 1

HYDRODYNAMIC CELL CULTURE ENVIRONMENT FOR THREE DIMENSIONAL TISSUE GROWTH

FIELD OF THE INVENTION

The present invention relates a novel hydrodynamic cell culture environment that uniquely combines boundary layer perturbations, enlarged surface area for gas transfer, and hydrodynamic flow to enhance gas mass transfer and suspend cells growing in 3-dimensions. Fabricated from flexible gas permeable compliant materials, walls freely move with rotation thereby enhancing cellular suspension. It is low cost and universally useful for carrying out 3-dimensional cell and tissue culture processes.

BACKGROUND OF THE INVENTION

The culture process for mammalian cells, animal cells, insect cells, bacteria, yeast and molds has one major rate limiting step, oxygen mass transfer. Oxygen metabolism is essential for metabolic function. In mammalian and animal cell culture it is especially important during the early stages of rapid cell division. Oxygen utilization per cell is greatest when cells are suspended; requirements decreasing as the cells aggregate and differentiate. However, during the later phases of cell culture, as the number of cells per unit volume increases, the bulk oxygen mass transfer requirements increase. Traditionally, increased requirements are accommodated by mechanical stirring methods. The present invention both randomizes the hydrodynamic flow, disrupts the establishment of boundary layers, enlarges the gas transfer surface area, and enhances mass transfer while allowing 3-dimensional tissue growth.

There are several basic strategies for increasing the gas mass transfer across a membrane: increase oxygen concentration; increase the rate of transfer from the air to the media; and/or increase the surface area for gas exchange. Increasing the oxygen partial pressure will increase the bulk oxygen transfer. However, a boundary layer of oxygen toxicity will form at the gas permeable membrane-media interface. Cells entering the toxic boundary layer could sustain irreparable damage. Approaches to increasing the rate of gas transfer at the air-membrane-media interface include: increase the rate of air movement across the membrane with air pumps or other mechanical means; increase the gas diffusion rate across the membrane by selecting a more gas permeable membrane; and/or increase the rate of media flow past the membrane. In each approach the rate of exchange across the gas permeable membrane is augmented, leading to improved gas exchange. The third approach for increasing bulk gas transfer is to increase the air-membrane-media surface area. An enlarged surface enhances the bulk gas transfer. Improved gas exchange serves to both increase oxygen availability and remove the carbon dioxide by-product. Carbon dioxide has a higher diffusivity constant in silicone material, gas permeable silicone membranes will more readily remove carbon dioxide.

The majority of mammalian and animal cells require cell-to-cell contact and 3-dimensional growth to differentiate into tissue. Recent technology has been established to grow mammalian cells in 3-dimensional constructs using rigid horizontally rotating bio-reactors developed by NASA, with forced air oxygenation through precision milled and drilled shafts. Such devices, having rigid non gas permeable walls defining the cell culture chambers are disclosed in U.S. Pat. No. 5,026,650, entitled "Horizontally Rotated Cell Culture System with a Coaxial Tubular Oxygenator", and U.S. Pat. No. 5,153,131, entitled "High Aspect Ratio Vessel and Method of Use." They are not adaptable for use with existing laboratory equipment, and require specific air pumps and have gas transfer rates that are limited. U.S. Pat. No. 5,330,908, "High Density Cell Culture System", discloses a process to increase the oxygenating surface area using a cell culture chamber that is rigid but oxygen permeable. However, all of the above horizontally rotating cell culture vessels have rigid walls that define the cell culture chamber and the stated invention is the establishment of a low shear quiescent microgravity like cell culture environment. As such, the rigid walls dampen all propagation waves, inhibiting both random hydrodynamic flow and gas mass transfer; now disclosed in the present invention.

All the current horizontal rotating cell culture systems developed by NASA strive to achieve a quiescent microgravity like environment, having origins in the NASA space program. There are over 100 scientific articles and abstracts demonstrating or suggesting microgravity induced aberrancy in cell growth, cell differentiation, cell movement, cell size and shape, cell physiology or general human physiology, occurring in their rotating culture systems or in actual microgravity. The normal mammalian hydrodynamic milieu differs from a quiescent microgravity like environment. In a natural environment, cells are constantly moved, pulled or forced to settled in different directions depending on the position of the organism, ie; standing, sitting or lying down. Movements from walking, running, and breathing agitate the cells from random directions, thereby adding shear and random hydrodynamic flow. An intrauterine environment is characterized by cells developing in amniotic fluid with random hydrodynamic flow, high mass transfer and defined by a compliant elastic uterus. The present invention more closely emulates the intrauterine hydrodynamic and gas mass transfer environment where positional changes, breathing, and movement continuously disrupt boundary layers and randomizes the direction of hydrodynamic flow. More specifically, the present invention relates to a novel hydrodynamic and gas exchange environment that suspends cells and facilitates 3-dimensional tissue growth.

PRIOR ART

Prior art includes the following patents and, the references cited therein.

U.S. Pat. No. 5,330,908 issued to G. F. Spaulding, on Jul. 19, 1994, relates to a rigid gas permeable horizontally rotating vessel with increased surface area for gas exchange. The gas permeable support structure is rigid and does not move to disrupt boundary layers. Internal dimensions are fixed. Cells are not agitated.

U.S. Pat. No. 5,153,131 issued to D. A. Wolf et. al., on Oct. 6, 1992, relates to having the surface area for oxygenation increased by use of a larger gas permeable membrane disposed over a screen and fixed to the rigid walls. They estimate that the membrane perpendicularly protrudes 1/20 of an inch through holes in the screen under hydrostatic weight thereby causing mixing without shear. The culture vessel is rotated so that the suspended cells are not agitated. The chamber dimensions are fixed and narrow. Oxygenation is via forced air through a precision milled and drilled center shaft. All surfaces, including the gas permeable membrane, are held substantially rigid. It is complicated to assemble and disassemble. The gas permeable membrane is held by a support structure that defines the chamber. Cells are suspended by rotation. In contrast to the above invention, the present invention has changing internal dimensions, agitates the cells, does not require a pump for oxygenation, facilitates random hydrodynamic flow, the oxygen permeable member defines the entire chamber and is the support structure, walls move in all directions, wall movement is variable and can exceed 1 inch in movement, and cells are suspended by rotation and wall movement.

U.S. Pat. No. 5,057,428 issued to S. Mizutani et. al. on Oct. 15, 1991, relates to a cylindrical bioreactor tank which is rotated about a horizontal axis. There is a cylindrically shaped mesh in the chamber which defines inner and outer chambers. A pipe conveys oxygen from an air pump into the chamber and a flow path is established to flow return pipes which provide for continuous replenishment of spent media. It has rigid walls. It is complicated to assemble and disassemble. U.S. Pat. No. 5,026,650 issued to R. P. Schwartz et. al. on Jun. 25, 1991, relates to a cylindrically formed cell culture chamber and system for mammalian cell growth which is rotated on a central horizontally disposed oxygenating shaft. The shaft has a gas permeable membrane glued to its surface which supplies oxygen to a liquid culture medium containing microcarriers and cells. Oxygenation is via forced air through a precision milled and drilled center shaft, the center shaft partly covered with a gas permeable membrane. The vessel is rotated such that there are no fluid shear forces generated by velocity gradients at the membrane-media boundary layer. All surfaces, including the gas permeable membrane, are held rigid. The culture vessel is rotated so that the suspended cells are not agitated. It is complicated to assemble and disassemble.

U.S. Pat. No. 5,015,585 issued to J. R. Robinson, on May 14, 1991, discloses a bioreactor construction utilizing a single polymer in a concentric geometric configuration to add durability and reduce complexity.

U.S. Pat. No. 3,821,087 issued to R. A. Rnazek et. al., on Jun. 28, 1974, discloses a cell growth system where cells are grown on membranes in a nutrient medium. Nutrient fluids carrying oxygen flow through the vessel and pass through a membrane to contact the cell culture. The fluid is driven by an impeller into the culture vessel. Numerous capillaries are used to distribute oxygen and nutrients over a large area to reduce uneven distribution of resources. There is no rotation of the vessel. It is complicated to assemble and disassemble.

U.S. Pat. No. 4,749,654 issued to D. Karrer et. al., on Jun. 7, 1988, relates to a cell growth system using gas permeable membranes and a waste gas removal system. A stirrer is used for agitation. Oxygen flows in through one side of the membrane and carbon dioxide flows out the other side.

U.S. Pat. No. 4,948,728 issued to G. Stephanopauous et. al., on Aug. 14, 1990, discloses a porous ceramic material with a plurality of flow passages. A biofilm is in contact with an inner wall and a gas permeable membrane covers the outer wall. An oxygen flow along the outer wall permeates the membrane and ceramic housing to reach biomaterial. Nutrients flow along the inner wall in direct contact with the biofilm. There is no rotation of the vessel.

U.S. Pat. No. 4,962,033 issued to J. M. Serkes, on Oct. 9, 1990, is an example of a cell culture roller bottle which has rigid walls that are not gas permeable.

U.S. Pat. No. 4,391,912 issued to K. Yoshida et. al., on Jul. 5, 1983, is an example of a cell culture system with hollow fibers that is not rotated.

SUMMARY OF THE PRESENT INVENTION

In the present invention, the cell culture chamber is defined by two gas permeable membranes with a hypodermic syringe port. The port is of a similar construct found associated with standard intravenous tubing. A hypodermic syringe port enables the introduction of fresh nutrients and the withdrawal of spent nutrients. The gas permeable membrane that defines the culture chamber, is compliant, non-rigid, of teflon or silicone material. It is disposed, by the edges of the cell culture chamber, to a horizontally rotating disk, such as is found in a standard tissue culture laboratory. Internal dimensions can range from 0 at the seams to over an inch in the center.

In constructing the culture vessel, two flat compliant sheets of teflon or silicone with an appropriate wall thickness are placed on top of one another. The thickness is calculated based on the desired diffusion constants, which are known in the art, and is typically less than 0.050 inches thick. The edges of the two sheets are glued or fused together using conventional methods that are known in the art. In one seam, a hypodermic syringe port is introduced between the membrane sheets, and is glued or fused into the seam. The port, seam and membrane sheets define a compliant cell culture chamber that retains cell culture media.

In rotating the culture vessel, the edges of the cell culture chamber, beyond the seams, serve as points of attachment to a horizontally rotating drive means. Clamps, wires, hooks, pins or other means of mechanical attachment dispose the cell culture chamber to a horizontally rotating means such as a disk. The disk can be constructed of a wire mesh, metal frame with holes or any rigid frame that will support the cell culture chamber without blocking air flow over the membrane surfaces. Media and cells are introduced into the chamber defined by the gas permeable membranes through the hypodermic syringe port. The chamber is filled until there is zero head space and the cell culture chamber becomes taut.

In the oxygenation of the culture, gas mass transfer is facilitated by wall movement. The compliant gas permeable membranes which define the cell culture chamber move under the weight of the media during rotation. Gas mass transfer is enhanced by disturbing the boundary layers that are established at the air-membrane membrane-media, and cell-media interfaces. If left undisturbed, gas gradients would form in the boundary layers and reduce the rate of gas exchange across the membrane and cell interfaces. Both bulk gas transfer and rate transfer are facilitated by wall movement. With wall movement there is a fluid shift in the cell culture chamber. The fluid shift yields random hydrodynamic fluid streamlines which are propagated throughout the cell culture chamber, enhancing mass transfer. Each disk rotation changes the propagation vector for fluid streamlines by 360° causing agitation. Thus, wall movement facilitates gas mass transfer by both boundary layer disruption and bulk agitation. This is in contrast to other horizontally rotating, zero head space vessels that define their inventions as decreasing or eliminating the velocity gradients and agitation.

In agitating cells, wall movement from alternating directions yields fluid stream lines that agitate and suspend cells. Bulk wall movement dissipates fluid shear over a larger area as opposed to compressed shear gradients that are generated by stirring or air sparging. The mild cell agitation disrupts boundary layer gradients that are continuously create at outer surface of a cell or tissue aggregate. Disrupting cell-media boundary layers facilitates the mass transfer of both nutrients and gas. Facilitated transfer allows tissues to grow 3-dimensionally to higher densities and with improved fidelity.

For processing mammalian and animal cells, Cells are isolated by conventional means or purchased commercially, for example from American Tissue Culture Corporation, Rockville Md. The cell culture chamber is sterilized and fresh media and cells are admitted to completely fill the cell culture chamber, zero head space. Air bubbles would substantially increase hydrodynamic shear and are purged from the chamber. The cell culture chamber is horizontally rotated to suspend and agitate the cells, allowing 3-dimensional growth. In the present invention, rotation enhances mass transfer of gas across the gas permeable membrane. Both oxygen and carbon dioxide are equilibrated across the membrane with the surrounding atmosphere. When the nutrients are depleted, the rotation is stopped and the cells allowed to sediment to the bottom of the culture chamber. Cell free nutrient depleted media is withdrawn through the hypodermic syringe port and replaced with fresh media. After repletion with fresh media, the cells are resuspended by rotation and wall movement agitation.

The present invention provides a novel fluid dynamic environment embodied in a cell culture chamber and processes for 3-dimensional tissue culture. Enhanced gas mass transfer supports the maintenance of higher density cell culture or more metabolically active cells. It will be appreciated that the cell culture system is simple to construct, low cost and can be widely used by existing laboratories with conventional equipment.

DESCRIPTION OF THE DRAWINGS

In the drawings:

FIG. 1 shows a perspective view of the general organization of the present invention; and FIG. 2 shows a schematized cross sectional view of the cell culture chamber disposed on a horizontally rotating disk.

DESCRIPTION OF THE PREFERRED EMBODIMENT

Referring now to FIG. 1, the general organization of the present invention is illustrated. A horizontally rotating disk 1 is shown with the cell culture chamber 6 as defined by gas permeable membranes 2 attached by hooks/attachment points 4. The rotating disk 1 is a commonly used laboratory device for rotating test tubes. A suitable rotating device is available from VRW Scientific, New York, N.Y., catalog no. RD4512. Speeds can be adjusted manually to achieve proper cell suspension. The cell culture chamber is filled or evacuated through the hypodermic syringe port 3.

Referring now to FIG. 2, the schematized cross sectional view shows juxtaposition of the cell culture chamber 6 defined by gas permeable membranes 2 to the rotating disk 1 and horizontal axis 7. The gas permeable membranes 2 that define the cell culture chamber 6 also provides attachment points 4 to the rotating disk 1. Membranes 2 are attached 4 via hooks 4 to the horizontally rotating disk 1 so that there is an air gap 5 between the membranes 2 and the disk 1. The points of attachment 4 were aligned so to center the cell culture chamber 6 with the center of horizontally rotating disk 1 and over the centroid of the horizontally rotating axis 7. Media and cells are contained within the cell culture chamber 6. Gas permeable membranes 2 which define the cell culture chamber 6 can be constructed from a variety of compliant materials that have suitable gas transfer characteristics. Such materials are commonly known in the cell culture art and to food wrapping manufactures; gas transfer constants are listed in reference books. A suitable reference source for diffusion constants of gases through different materials can be found in the CRC Handbook, CRC Press, Boca Rotan, Fla. Alternatively, gas permeable cell culture bags can be purchased commercially from Baxter Scientific, McGaw Park, Ill., and are suitable for the disclosed invention. In the preferred embodiment, gas permeable membranes 2 are constructed from silicone or teflon. The cell culture chamber can be fabricated into a variety of different shapes including; a square cell culture chamber, a round cell culture chamber, an octagonal cell culture chamber with multiple attachment points, and a cylindrical cell culture chamber, each representing alternative embodiments.

As an example of use of the cell culture system, Ham's F10 media can be sterilized and placed into the cell culture chamber. A hypodermic syringe can be used to inject media innoculated with isolated mammalian cells through the hypodermic syringe port into the chamber. The cell culture chamber is completely filled with cells and media, with zero head space. Such cells are commercially available, being Baby Hamster Kidney (BHK) cells which can be obtained from American Tissue Culture Corporation (ATCC, Rockville, Md.). After cells are injected into the cell culture chamber, excess bubbles are removed. Cell culture chamber volumes can range from less that 1 ml to several liters. To provide the necessary ambient environment, the cell culture system is placed into a conventional incubator where it rotates and wall movement supports the growth of 3-dimensional cellular aggregates.

Cell are suspended by adjusting the rotating speed until wall movement suspends cells throughout the media. After the cells metabolize the media nutrients, spent cell culture media is removed and replaced with fresh media to sustain growth. Typically, mammalian and animal cells will grow and aggregate in suspension. Cellular aggregates can range from 50 microns to 3 cm. As the cells aggregate they form an extracellular matrix upon which cells adhere, differentiate and become 3-dimensional tissue. Three dimensional aggregates display many of the biochemical and morphological features found in the primary tissue from which the cell isolates were derived.

The present invention improves the gas mass transfer rates across the air-membrane-media and cell-media boundary layers. Wall movement resulting from the weight of the media against the elastic and compliant gas permeable membrane disrupts the boundary layer causing agitation. Agitation reduces the gas gradient that builds up in the air-membrane, membrane-media, and cell-media boundary layers. The gas transfer rate is governed by gas partial pressures at each surface of the membrane. As the partial pressure difference increase the rate of gas exchange decreases. Therefore, wall movement decreases the partial pressure difference at the membrane by decreasing the magnitude of the boundary layer gradients hence increasing the rate of gas exchange. A second consequence of wall movement is hydrodynamic agitation. Bulk fluid movement, and the fluid streamlines created therein, augment the bulk transfer of gas throughout the media. Bulk agitation over a large surface area reduces the magnitude of hydrodynamic shear per unit cell area when compared to impeller or gas sparged systems. The net result is enhanced oxygen transfer through agitation, and an enhanced ability to support 3-dimensional tissue growth.

EXAMPLE 1

A cell culture chamber is made of Teflon FEP fluorocarbon film, 5 mil/125 μm thick, purchased from American Fluoroseal Corporation, Columbia, Md. The listed volume of the bag is 7 ml but the volume required to full the chamber without leaving an air bubble is usually in excess of 10 ml. Each bag has a syringe port of fluorinated ethylene propylene extruded tubing with a polypropylene female luer lock and cap. Bags are autoclavable. According to data furnished by the manufacturer the permeability rate of Teflon FEP fluorocarbon film, 1 ml/25 μm thick at 25° C. is $11.6 \times 10^3$ $cm^3/(m^2 \cdot 24h \cdot atm)$ for oxygen and $25.9 \times 10^3$ $cm^3/(m^2 \cdot 24 hr \cdot atm)$ for carbon dioxide. The cell culture chamber is disposed to a 14.5 cm perforated disk that is rotated about a horizontal axis by a motor. The cell culture chamber is filled by syringe with a monodispersed cell suspension containing 0.5–1.5 million cells per ml of medium appropriate for the cell line. Mammalian cells are isolated by conventional methods or purchased commercially. The chamber is manipulated as necessary during filling to force out air bubbles that tend to collect at the chamber edges. The filled chamber is disposed to the disk by means of rubber bands; the motor/disk assembly is placed in a $CO_2$ tissue culture incubator (3–5% $CO_2$ depending upon the buffering capacity of the medium) at 37° C. Rotation is started at approximately 15 rpm by visually timing the number of rotations per minute and adjusting the motor speed. Small cell aggregates usually form within a few hours and larger aggregates gradually develop thereafter. As the aggregates increase in size they resemble spheroids. The size and shape of the spheroids that develop vary among cell lines. As larger spheroids develop, either by growth or by fusion of small aggregates, the rate of rotation is adjusted as necessary to maintain the particles in suspension. Microcarrier beads may be included for attachment and support. To feed the cultures, some of the medium is removed by syringe and replaced with fresh medium. The culture chamber is removed from the disk, held upright for a minute or two until cells begin to settle, and supernatant medium is carefully aspirated into a sterile syringe. If a cell sample is to be removed, the aspiration is done before the cells settle. Typically, approximately 7 ml of medium is removed and replaced with fresh medium each day. The culture may be continued for many weeks depending upon the design of the experiment. Cells are harvested by aspirating the contents of the culture chamber or, if the cell masses are too large, by cutting the culture chamber and poring out the contents. If the cell masses are to be sectioned they are immediately fixed. Aliquots may be taken before fixation for dissociation, subculture, single cell counting and analysis or other studies as required. The cell types cultured in the present invention are given in Table 1 which shows that all cell types cultured as monolayers were also successfully cultured in the rotating bags. Table 2 illustrates important cytochemical markers are expressed by cells cultured in the present invention, compared to conventional monolayer culture.

TABLE 1

| Growth of various cell lines | | |
| --- | --- | --- |
| Cell Type | Monolayer Culture | Rotating Disk |
| Gliomas | | |
| 01-T | + | + |
| HBR 9 | + | + |
| HBR 65 | + | + |
| HBR 84 | + | + |
| HBR 147 | + | + |
| Bladder Cancer | | |

TABLE 1-continued

| Growth of various cell lines | | |
| --- | --- | --- |
| Cell Type | Monolayer Culture | Rotating Disk |
| HBL 2 | + | + |
| J82 | + | + |
| Prostate Cancer | | |
| PC3 | + | + |
| LNCaP | + | + |
| DU 145 | + | + |
| Prostate fibroblasts | | |
| NF2 | + | + |
| NPF-209 | + | + |
| Pancreatic Cancer HS-766T | + | + |
| Brain metastasis HBM-10 | + | + |

TABLE 2

| Antigen Expression | | | |
| --- | --- | --- | --- |
| Cell Line | Cytokeratin | CD44 | E Cadherin |
| Glioma - HBR 84 | | | |
| Monolayer | | — | |
| Agitated Culture | | 3–4+ | |
| Bladder Cancer - HBL2 | | | |
| Monolayer | — | 1+ | |
| Agitated Culture | 4+ | 2–3+ | |
| Bladder Cancer - J82 | | | |
| Monolayer | 1–3+ | | 1+ |
| Agitated Culture | 3–4+ | | 2–3+ |
| Prostate Cancer - PC3 | | | |
| Monolayer | — | | |
| Agitated Culture | 4+ | | |
| Prostate Cancer - LNCaP | | | |
| Monolayer | | + | 1+ |
| Agitated Culture | | 3–4+ | 3–4+ |

The process of choosing a cell type(s) and growing the cells into 3-dimensional aggregates constitutes tissue engineering. Cellular aggregates derived from the present invention have broad utility. Sizes and shapes vary and can take the form of cellular aggregates or, sheets of cellular and extracellular material. The present invention can be used to expand a population of normal human cells into a larger population. That expanded cell population would be useful for transplantation back to the original host or to a different tissue compatible host. Additionally, the engineered tissue can be used for research; testing gene therapies, viral propagation, new drug treatments and/or for testing fundamental biological theory.

It can be appreciated that the maintenance of a normal metabolic environment, through enhanced gas mass transfer in the present invention, would improve the scientific capability for engineering tissues. Costs and FDA compliance are significantly improved by using disposable cell culture chambers and standard rotating devices.

It will be apparent to those skilled in the art that various changes may be made in the invention without departing from the spirit and scope thereof, and therefore the invention is not limited by that which is disclosed in the drawings and specifications but only as indicated in the appended claims.

I claim:

1. A method of oxygenating cells in a culture medium comprising the steps of:

providing a culture chamber defined between two compliant membrane walls each gas permeable, filling the culture chamber with a culture media containing cells to have a zero head space and disposing the culture chamber on a rotating disk drive means in an incubator for rotation about a horizontal axis of the disk, rotating the culture chamber about its horizontal axis at a rotational speed adequate to suspend the cells in the culture media for cell growth, oxygenating the culture media through the two compliant membrane walls each gas permeable by exposure of the two walls to the atmosphere, and adding fresh culture media and withdrawing spent culture media from the culture chamber to maintain cell growth during incubation.

2. The method as set forth in claim 1 wherein said compliant membrane walls each gas permeable of said culture chamber are constructed from silicone material.

3. The method as set forth in claim 1 wherein said compliant membrane walls each gas permeable of said culture chamber are constructed from teflon material.

4. Apparatus for oxygenating cells in a culture medium comprising:

means defining a culture chamber between two compliant membrane walls each gas culturing chamber means including two compliant membrane walls, each gas permeable, means for mounting said chamber means on a horizontally rotating disk drive, means for adding fresh culture media and for withdrawing spent culture media from the chamber means;

disk drive means for horizontally rotating said chamber means at a rotational speed adequate to suspend cells in the chamber means when filled with cell-containing media;

wherein said chamber means is constructed so that when filled with cell-containing media to have a zero head space and mounted on said disk drive means said compliant membrane walls are exposed to the surrounding atmosphere so that the media can be oxygenated.

5. The apparatus as set forth in claim 4 wherein said compliant membrane walls are constructed from silicone material.

6. The apparatus as set forth in claim 4 wherein said compliant membrane walls are constructed from teflon material.

7. A process for producing aggregates of mammalian cells comprising:

isolating mammalian cells, inoculating the isolated mammalian cells into a culture media, providing a culture chamber defined between two compliant membrane walls each gas permeable, filling the culture chamber with a culture media containing said isolated mammalian cells to have a zero head space and disposing the culture chamber on a rotating disk drive means in an incubator for rotation about a horizontal axis of the disk, rotating the culture chamber about its horizontal axis at a rotational speed adequate to suspend the isolated mammalian cells in the culture media for cell growth, oxygenating the culture media through the two compliant membrane walls each gas permeable by exposure of the two walls to the atmosphere, adding fresh culture media and withdrawing spent culture media from the culture chamber to maintain cell growth during incubation, and maintaining culture conditions whereby three dimensional tissue growth is achieved thereby producing aggregates of mammalian cells.

* * * * *